(12) United States Patent
Holmqvist (10) Patent No.: US 9,700,709 B2
(45) Date of Patent: Jul. 11, 2017

(54) COUPLING ARRANGEMENT

(75) Inventor: Anders Holmqvist, Värmdö (SE)

(73) Assignee: SHL Group AB, Nacka Strand (SE)

(*) Notice: Subject to any disclaimer, the term of this patent is extended or adjusted under 35 U.S.C. 154(b) by 152 days.

(21) Appl. No.: 13/982,917

(22) PCT Filed: Jan. 26, 2012

(86) PCT No.: PCT/SE2012/050073
§ 371 (c)(1),
(2), (4) Date: Aug. 15, 2013

(87) PCT Pub. No.: WO2012/105892
PCT Pub. Date: Aug. 9, 2012

(65) Prior Publication Data
US 2013/0313823 A1    Nov. 28, 2013

Related U.S. Application Data

(60) Provisional application No. 61/437,844, filed on Jan. 31, 2011.

(30) Foreign Application Priority Data

Jan. 31, 2011  (SE) ...................................... 1150064

(51) Int. Cl.
*A61M 39/10* (2006.01)
*A61M 5/31* (2006.01)
*A61M 5/24* (2006.01)

(52) U.S. Cl.
CPC ...... *A61M 39/1011* (2013.01); *A61M 5/3129* (2013.01); *A61M 2005/2488* (2013.01);
(Continued)

(58) Field of Classification Search
CPC ............ A61M 39/1011; A61M 5/3129; A61M 2005/3142; A61M 2039/1033; A61M 2005/2488
(Continued)

(56) References Cited

U.S. PATENT DOCUMENTS 4,108,202 A * 8/1978 Schoepe ........................ 137/436
4,659,119 A * 4/1987 Reimert ......................... 285/82
(Continued)

FOREIGN PATENT DOCUMENTS

GB         2353078 A  *  2/2001  ............ A61M 5/347
WO     2005/044348 A1     5/2005

OTHER PUBLICATIONS

Sweden Patent Office, Int'l Search Report in PCT/SE2012/050073, Apr. 17, 2012.

*Primary Examiner* — James M Hewitt
(74) *Attorney, Agent, or Firm* — Piedmont Intellectual Property (57) ABSTRACT

A coupling arrangement in a medicament delivery device, the coupling arrangement being adapted to permanently attach a first and a second longitudinally elongated tubular component to each other. The coupling arrangement includes a first positive connection mechanism configured to lock the first and the second components to each other such that the components are locked from being moved in a longitudinal direction in relation to each other, and a second positive connection mechanism configured to lock the first and the second components to each other such that the components are locked from being rotated in relation to each other about a longitudinal axis of the components.

12 Claims, 6 Drawing Sheets

(52) U.S. Cl.
CPC ............... *A61M 2005/3142* (2013.01); *A61M 2039/1033* (2013.01)

(58) Field of Classification Search
USPC .......................................................... 285/92
See application file for complete search history.

(56) References Cited

U.S. PATENT DOCUMENTS

| | | | |
|---|---|---|---|
| 4,757,593 A * | 7/1988 | Pallini et al. .................... | 29/432 |
| 5,906,398 A * | 5/1999 | Larsen et al. .................... | 285/24 |
| 6,981,547 B2 * | 1/2006 | Maguire et al. ........... | 166/242.7 |
| 7,258,119 B2 | 8/2007 | Mazzoni | |
| 7,618,072 B2 * | 11/2009 | Funamura .......... | A61M 39/1011 285/386 |
| 7,708,714 B2 * | 5/2010 | Connell ................ | A61M 1/285 604/30 |
| 7,758,548 B2 | 7/2010 | Gillespie et al. | |
| 8,372,057 B2 * | 2/2013 | Cude ..................... | A61M 39/10 604/240 |
| 2004/0127858 A1 * | 7/2004 | Bendek ............. | A61M 5/31541 604/208 |
| 2010/0268169 A1 | 10/2010 | Llewellyn-Hyde et al. | |

* cited by examiner

Fig. 4

COUPLING ARRANGEMENT

TECHNICAL FIELD

The present invention relates to a device for permanently attaching two components to each other, for example two housing parts that may be comprised in a medicament delivery device.

BACKGROUND OF THE INVENTION

There are a large number of devices and products where two or more components are to be connected and attached to each other, preferably in a non-reversible manner. This could for example be the case for a device comprising an outer housing having a number of components arranged inside said housing. For various reasons, the housing may comprise a number of housing parts. This could for example be the case when assembling and placing the components inside the housing, which is facilitated or enabled by dividing the housing into several housing parts.

When the housing parts are to be attached to each other, it is often desirable to have a connection between the parts that on the one hand makes it relatively easy to assemble the parts and on the other hand makes the connection irreversible. That is, it should not be possible to disconnect the housing parts from each other at least not without using excessive force.

On the other hand, when manufacturing parts that are made of plastic material and produced with standard injection moulding techniques, the geometries and the designs of attachment members must not be too complex and/or too many, since this would adversely affect the moulding forms and the use and complexity of mould cores, just to mention a few aspects.

Document WO2005/044348 discloses a common attachment solution where the parts to be connected are tubular with a generally circular cross-section. One housing part is arranged with a number of circumferentially extending recesses or grooves on its inner surface and the other housing part is arranged with a number of circumferential, radially extending protrusions on its outer surface, where the protrusions have profiles which are complementary to the shapes of the grooves. When assembling the two housing parts, the two parts are pushed together. The protrusions will then press radially on the inner surface of the housing part with the grooves until the protrusions enter the grooves and the two parts are locked together.

Even if this connection works well there are a number of drawbacks. A major drawback is that it requires quite a lot of force because of the friction between the protrusions and the inner surface of the housing part when the housing parts are pushed together. This pushing action thus requires some flexibility of the protrusions as well as the housing parts in the radial direction in order to enable the connection, but even so, there is a pronounced risk of permanent deformation of components due to the force exerted between them. On the other hand if the dimensions are chosen such that the radial force between the protrusions and the housing part is lowered, there is a risk that the final connection is not tight enough and that there may even be play in the connection if the tolerances are not small enough.

BRIEF DESCRIPTION OF THE INVENTION

The aim of the present invention is to remedy the drawbacks of the state of the art and to provide a device that securely locks interlocking components of a device to each other in a safe and tight way without the risk of permanent deformation of components and without the possibility of subsequent disconnection without damaging the components.

This aim is obtained by a device with the features according to the independent patent claim.

Preferable features of the present invention form the subject of the dependent patent claims.

According to a main feature of the invention it is characterised by a coupling arrangement in a medicament delivery device, said coupling arrangement being adapted to permanently attach a first and a second longitudinally elongated tubular component to each other, wherein the coupling arrangement comprises first positive connection means configured to lock the first and the second components to each other such that the components are locked from being moved in a longitudinal direction in relation to each other, and a second positive connection means configured to lock the first and the second component to each other such that the components are locked from being rotated in relation to each other about a longitudinal axis of the components.

According to another aspect of the invention the first positive connection means comprises a first attachment means, a first stop member, a second attachment means and a second stop member, and wherein the second positive connection means comprises a first locking means and a second locking means.

According to yet another aspect of the invention the first attachment means, the first locking means and the first stop member are arranged to said first component in a proximal end section, and wherein the second attachment means, the second locking means and the second stop member are arranged to said second component in a distal end section.

According to a further aspect of the invention the first attachment means is arranged in the form of at least one first structure which extends helically in a circumferential and longitudinal direction, wherein the second attachment means is arranged in the form of at least one second structure which extends helically in a circumferential and longitudinal direction.

According to yet a further aspect of the invention the first stop member is arranged in the form of a first annular surface facing the proximal direction and the second stop member is arranged in the form of a second annular surface facing the distal direction.

According to another aspect of the invention the at least one first structure is configured in the form of a protrusion or a groove and wherein the at least one second structure is configured in the form of a protrusion or groove complementary to the form of said first structure.

According to yet another aspect of the invention the at least one first and at least one second structures are arranged with complementary attachment surfaces that face each other in generally opposite longitudinal directions such that said complementary attachment surfaces abut each other when the components are attached to each other.

According to a further aspect of the invention said complementary attachment surfaces are arranged generally parallel to a radial plane.

According to yet a further aspect of the invention said complementary attachment surfaces are arranged inclined in relation to a radial plane of the components, such that undercuts are formed.

According to another aspect of the invention the first locking means is configured to form at least one first longitudinally elongated structure and wherein said second locking means is configured to form at least one second longitudinally elongated structure.

According to yet another aspect of the invention the locking means are configured in the form of complementary shapes such that said elements are capable of mating with each other to form said second positive connection when the components are attached to each other.

According to a further aspect of the invention the first locking means is configured in the form of a male or a female structure and wherein the second locking means is configured in the form of a male or female structure complementary to the form of said first locking means.

According to yet a further aspect of the invention the first and the second locking means are configured in the form of ratchets having complementary shapes.

There are a number of advantages with the present invention. Due to the fact that the first attachment means extends helically, the radially directed contact force between the components will be distributed in the longitudinal direction of the components and not along the circumference only, as with conventional devices. This feature greatly reduces the risk of permanent deformation of the components during attachment.

Because the first and second attachment means have complementary shapes, a first positive connection (form-locking) between the components is obtained, providing a very firm attachment in the longitudinal direction due to the helical extension of the attachment means.

In order to ascertain that the components cannot be disconnected from each other by turning them relative to each other, locking means are arranged on the two components. Since these also have complementary shapes, a second positive connection between the components is obtained, providing a firm attachment also in the circumferential/rotational direction, such that the components are locked from being rotated in relation to each other about a longitudinal axis.

Thus, the attachment means in combination with the locking means according to the invention provide a very firm attachment of the two components. In one preferred embodiment the attachment surfaces of the attachment means are arranged generally perpendicular to the longitudinal direction of the components, providing parallel attachment surfaces that abut each other for improved attachment. In order to increase the attachment between the two components, the attachment surfaces may be arranged with undercuts. This will further increase the locking action between the two components by providing a hooking engagement between the surfaces.

The locking means are preferably arranged with complementary surfaces that will provide a positive connection (form-locking action) between the two components against any attempts to rotate them relative to each other. The locking means could have many different shapes that provide the desired function.

These and other aspects of and advantages with the present invention will become apparent from the flowing detailed description of the invention and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

In the present application, the term "distal part/end/direction" refers to one specific part/end of the device, or direction to that part/end; or the parts/ends of the members thereof. Distal is marked D in FIG. 1. Correspondingly, the term "proximal part/end/direction" refers to a specific part/end of the device, or directions to that part/end; or the parts/ends of the members thereof, which are located at the opposite end of the device in relation to the distal end. Proximal is marked P in FIG. 1.

Further, the term "longitudinal" with or without "axis", when used, refers to a direction or an axis through the device or components thereof in the direction of the longest extension of said device or said components.

In a similar manner, the term "transversal" with or without "axis" refers to a direction, a plane or an axis through the device or components thereof in a direction generally perpendicular to the longitudinal direction.

A positive connection (also called form-locked) is herein defined as a mechanical connection between two components that do not rely on friction or gravity to stay connected. This means that the shapes of the interacting parts of the components are such that they are mutually engaging and block a disconnecting movement of the components in at least one direction.

The term "complementary shapes" used herein is defined as a mechanical connection between two components whose shapes are adapted to fit each other along a substantial part of their surfaces, e.g. such as the edges of the pieces of a jigsaw puzzle.

Also, if nothing else is stated, in the following part of the detailed description wherein the mechanical structure of the device and the mechanical interconnection of its components are described, the device according to the invention is in an initial non-activated or non-operated state.

Mechanical Structure of an Embodiment of a Device

The figures show two components or parts 10, 12 that are to be inter-connected or attached to each other by the present invention. In the figures shown, the components 10, 12 have a generally tubular form along a longitudinal axis 14, with generally circular cross-sections as seen in a plane transversal to the longitudinal axis and in particular in the respective areas of the components that are to be attached to each other. Also, even though the components shown have circular cross-sections, it is conceivable that the cross-sections may be somewhat different, such as oval. However, it is preferred that the cross-sectional shape is generally circular for reasons that will be explained below. One exemplary type of component where the present invention may be utilized is a housing part for a medicament delivery device, whereby the components 10, 12 will be referred to as the first and the second housing parts, respectively, in the following description.

Figure 1:
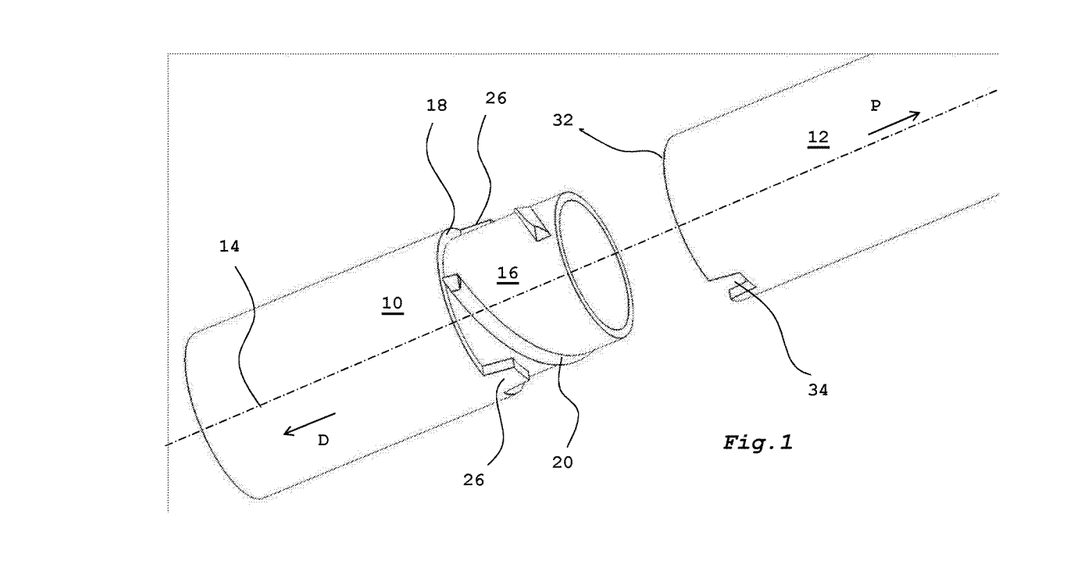
FIG. 1 is a perspective view of two components arranged with the present invention.

As seen in the figures, the first housing part 10 is arranged with a proximal end section 16, directed to the right in FIG. 1, hereafter named the proximal direction as indicated by arrow P in FIG. 1. The opposite direction will hereafter be named distal direction as indicated by arrow D in FIG. 1. The second housing part 12 is arranged with a distal end section 17, directed to the right in FIG. 2. All components and features of the device described hereafter will be referred to in relation to these directions. In the exemplary embodiment the diameter of the end section 16 is chosen somewhat smaller than the inner diameter of the distal end section 17 of the second housing part 12, such that the end section 16 may fit into the distal end section 17 of the second housing part 12. Obviously, it would be equally possible to have the diameter of the distal end section 17 chosen somewhat smaller than the inner diameter of the proximal end section 16 of the first housing part 10, such that the distal end section 17 would fit into the proximal end section 16 of the first housing part 10. Other configurations of the outer and inner diameters are also readily conceivable as long as one housing part may be inserted in the other housing part to establish the connection.

In the exemplary embodiment, the difference between the outer diameter of the end section 16 as compared to the outer diameter of the distal part of the first housing part 10 forms stop member 18 in the form of a first annular surface 18 facing the proximal direction.

Figure 3:
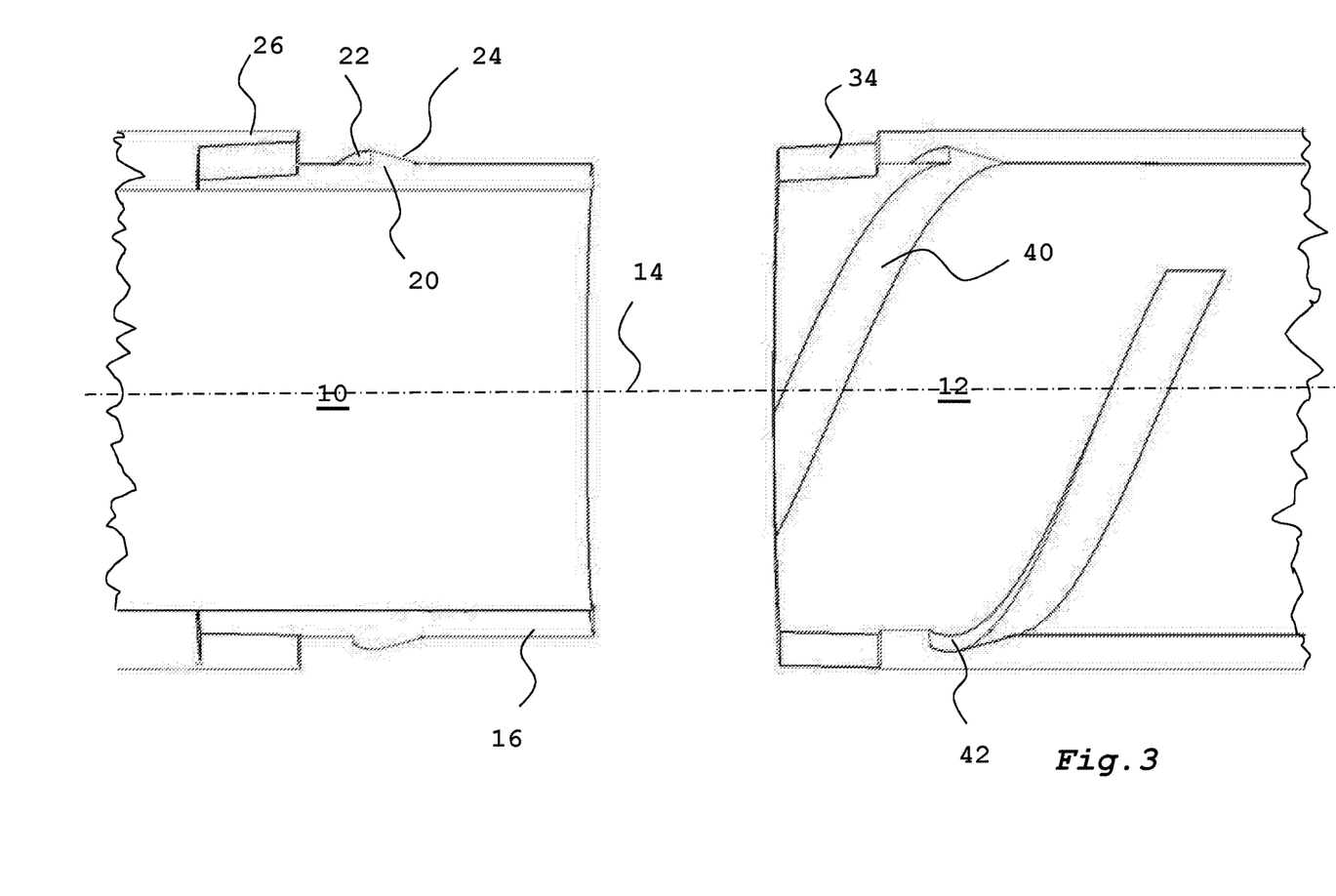
FIG. 3 is a detailed cross-sectional view along the longitudinal axis of FIG. 2, FIG. 4 schematically shows the effect on two components during attachment.

Further the outer surface of the end section 16 is in the exemplary embodiment arranged with a first attachment means, such as a first structure in the form of a protrusion 20, which protrusion has a helical extension of a certain pitch in a circumferential and longitudinal direction. The protrusion 20 further preferably has a certain profile as seen in a plane extending along the longitudinal axis 14 of the device. As seen in the cross-section of FIG. 3 the profile of the protrusion 20 comprises a first generally distally directed attachment surface 22, also extending generally parallel to a transversal plane of the first housing part 10, and a second transition surface 24 inclined in relation to the transversal plane, whereby the profile of the protrusion 20 obtains a general wedge shape.

Figure 4:
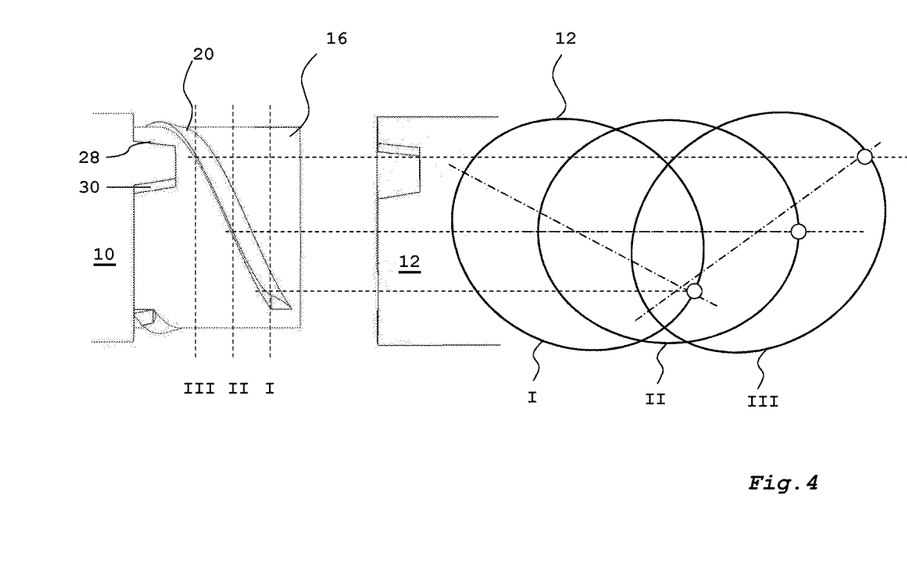

The first housing part 10 is in the exemplary embodiment further arranged with two first locking means 26, FIG. 1. Each first locking means 26 is formed by a longitudinally elongated structure, such as a tab, that extends in the proximal direction from the stop member 18 a certain distance into the end section 16. As seen in FIG. 4, side surfaces 28, 30 of the tab 26 are somewhat inclined in relation to the longitudinal direction, whereby the tab 26 has the appearance of a truncated wedge as seen in FIG. 4. The two tabs 26 are spaced 180 degrees in relation to each other around the circumference of the end section 16.

Figure 2:
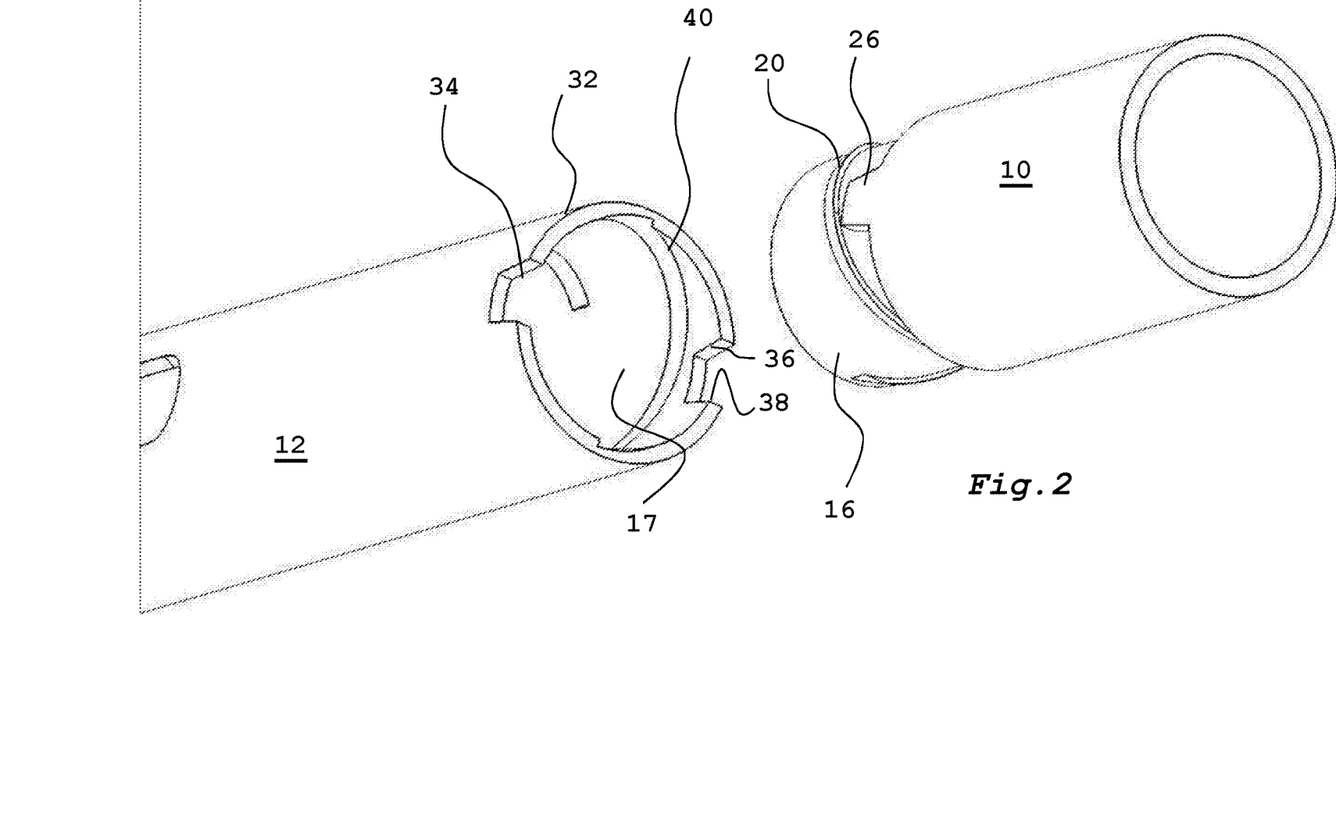
FIG. 2 is a perspective view corresponding to FIG. 1 but turned 180 degrees.

The distally directed end section 17 of the second housing part 12, FIG. 2, is arranged with two second locking means in the form of longitudinally elongated structures, in this exemplary embodiment referred to as cut-outs 34, which cut-outs 34 are spaced 180 degrees in relation to each other around the circumference of the distal end section 17 of the second housing part 12. Each cut-out 34 is arranged to interact with a corresponding tab 26 and is therefore provided with a shape complementary to the shape of the tabs 26, whereby the cut-outs 34 also are arranged with side surfaces 36, 38, FIG. 2, that are somewhat inclined in relation to the longitudinal direction of the housing parts. Obviously the first and second locking means may be configured in many different ways as long as they are longitudinally elongated and of complementary shapes, such as a male and a female structure.

The inner surface of the second housing part 12 at the distal end section 17 is further arranged with a second attachment means 40 in the form of a second structure, in this exemplary embodiment referred to as a groove, having a helical extension in a circumferential and longitudinal direction with a pitch that corresponds to the pitch of the protrusion 20 of end section 16 of the first housing part 10. The groove 40 may have a profile, as seen in a cross-section along the longitudinal axis 14, that is complementary to the profile of the protrusion 20; i.e. for example wedge-shaped with an attachment surface 42, FIG. 3. It is however to be understood that the profile of the groove 40 may differ from the profile of the protrusion as will be apparent below.

The arrangement of the first and second attachment means 20, 40 could be varied such that the protruding structure is arranged on the inner surface and the groove structure could be arranged on the outer surface.

Description of the Function and Operation of Said Embodiment

The exemplary embodiment of the present invention is intended to function as follows. When the two housing parts 10, 12 are to be permanently connected and attached to each other, the proximal end section 16 of the first housing part 10 is guided into the distal end section 17 of the second housing part 12. The most proximal part of the protrusion 20 and its radially outermost edge will come in contact with the inner surface of the distal end part of the second housing part 12, whereby a certain elastic deformation will occur such that the distal end of the second housing part will obtain a certain elliptic shape as seen in a cross-section transversal to the longitudinal axis. As seen in FIG. 4, due to the helical extension of the protrusion 20 the contact force on each cross-section will make the distal housing part elliptic, where the axis of the ellipse will have different directions depending on the position of the cross-section and the point of contact between the protrusion 20 and the inner surface of the distal end part of the second housing 12.

This is shown schematically in FIG. 4 where the left part shows imaginary cross-sections I to III and the right part shows the ellipses and their axes at the different cross-sections I to III. Thus, in contrast to the conventional circumferential protrusion, the helical protrusion according to the present invention will apply a point, or limited force as seen in each cross-section, instead of a force all around the circumference in each cross-section. This feature effectively prevents, or greatly reduces the risk of permanent deformation of the second housing part 12 due to the force from the protrusion.

When initially connecting the two housing parts, the tabs 26 of the first housing part 10 are preferably aligned with the cut-outs 34 of the second housing part 12.

Figure 5:
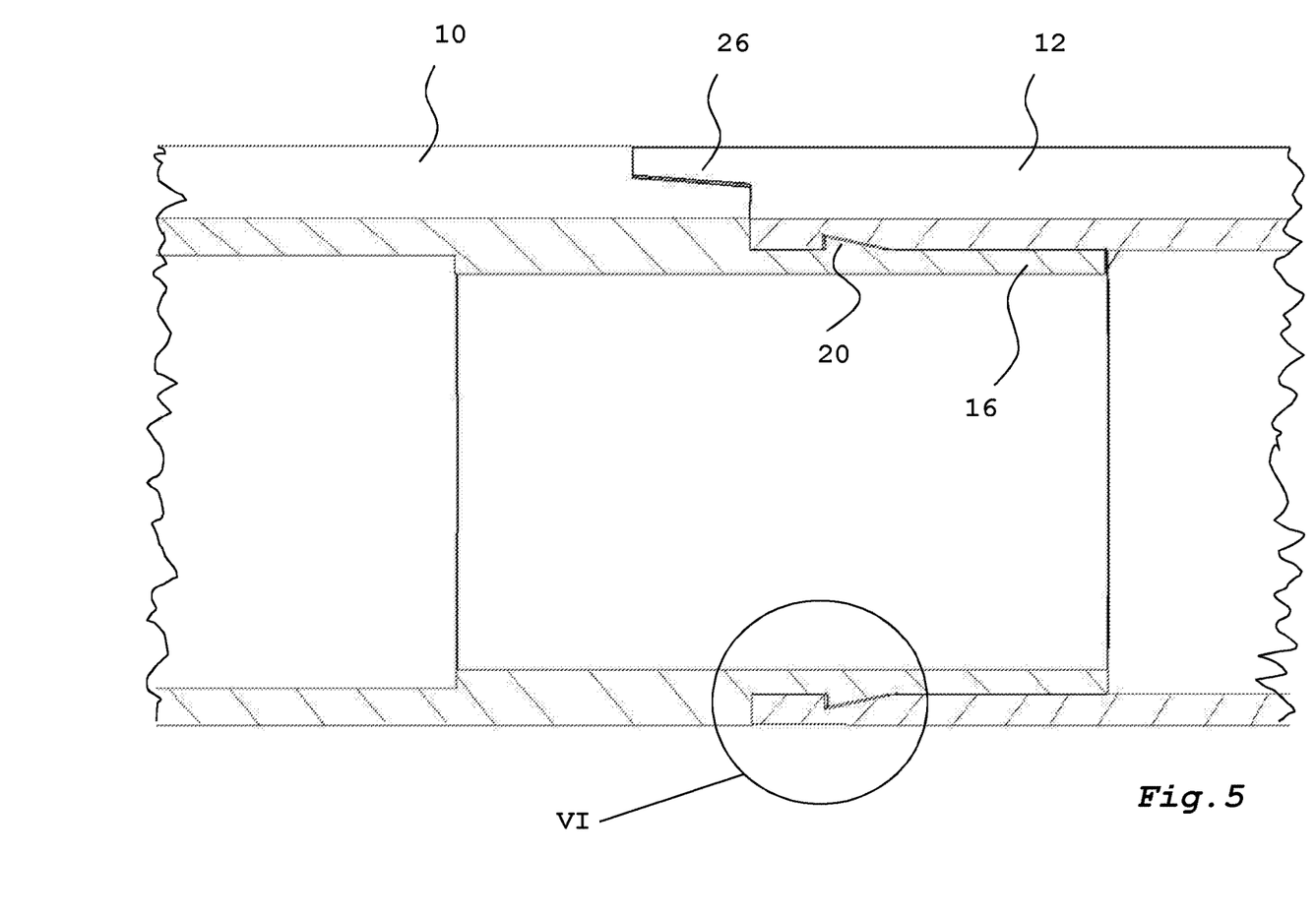
FIG. 5 is a detailed cross-sectional view of the two components of FIG. 1 when attached to each other, and FIG. 6a, b are detailed alternative embodiments of area VI, FIG. 5.
Figure 6A:
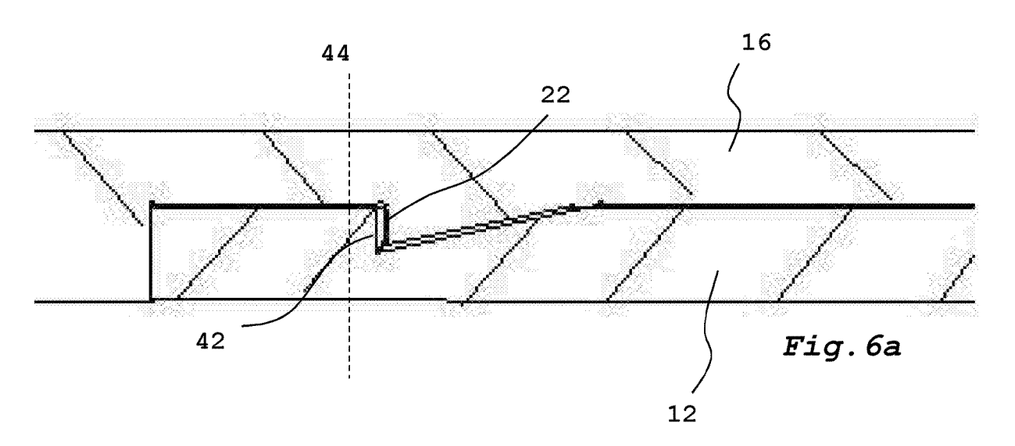

However, the two housing parts may also be turned in relation to each other during the connection sequence such that the tabs 26 are aligned with the cut-outs 34 towards the end of the sequence. In this respect, the turning is somewhat facilitated due to the helical extension of the protrusion 20. When the parts have been brought together such that the first stop member 18 of the first housing part 10 comes in contact with the second stop member 32, herein exemplified by a distally directed second annular surface of the second housing part 12, the protrusion 20 will fit into the groove 40 such that the two attachment surfaces 22, 42 will abut each other and thereby form a very strong connection between the two housing parts, FIG. 6a, that cannot be released without damaging the housing parts or its components. In addition to the very strong attachment between the two housing parts because of the protrusion and the groove, the tabs 26 have now been inserted into the cut-outs 34; FIG. 5, where the guiding of the tabs 26 into the cut-outs 34 has been facilitated by the inclined side surfaces 28, 30 of the tabs and the side surfaces 36, 38 of the cut-outs. The two positive connections between the two parts are now obtained in the longitudinal direction as well as in the circumferential direction.

Figure 6B:
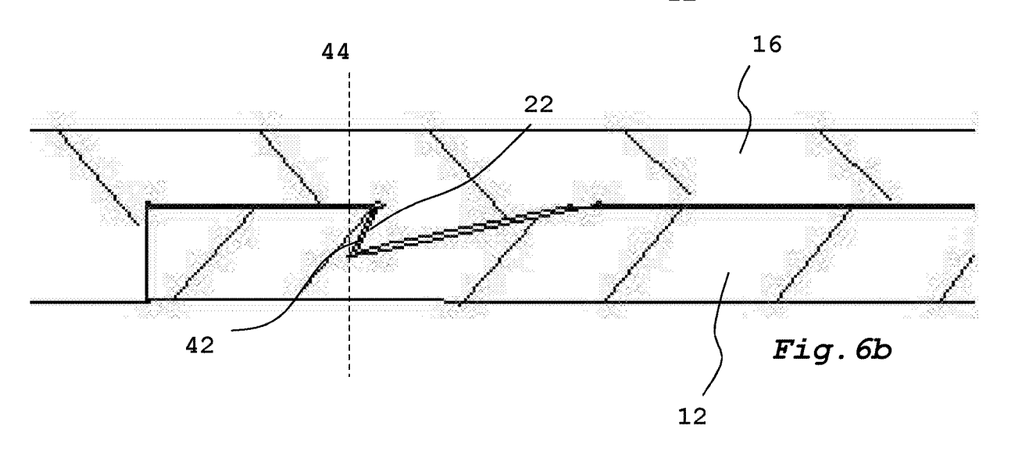

As described, a very strong connection is obtained, which is fairly easy to assemble without using excessive force to push the two parts together. The attachment and locking means can also be obtained by relatively simple and straightforward tools for injection molding. From the above it is quite clear that a strong attachment in the longitudinal direction is obtained by the attachment surfaces of the attachment means. If an even stronger connection is required, the attachment surfaces may be made inclined in relation to a radial plane 44 such that undercuts are created, as illustrated in FIG. 6b. Within the scope of the present invention, the number of protrusions/grooves may be modified, as well as the pitch, depending on the desired end result to be obtained. In this respect, it is feasible to have two or three protrusions extending helically around the outer surface of the end section 16. There will then be more than one contact point between the protrusions and the inner surface of the second housing part at each cross-section, but the resulting force is still lesser than the force from a circumferential protrusion.

To summarize, the first positive connection means comprises the first attachment means 20, the first stop member 18, the second attachment means 40 and the second stop member 32. The second positive connection means comprises the first locking means 26 and the second locking means 34.

As seen from the drawings and as understood from the description, the attachment surfaces are very important for forming the very strong first positive connection between the two housing parts. The transition surfaces are however not as important and may not necessarily be complementary, but may have other shapes depending on the application.

Within the scope of the present invention it is of course possible to design the locking means in other ways that still can perform a locking action in the circumferential direction between the housing parts when attached together. Instead of two tabs and two cut-outs, the locking means 26, 34 may be arranged in many different male-female configurations, such as a ratchet structure that can cooperate with a corresponding ratchet on the distally directed end surface of the second housing part 12.

Another solution is to provide the inner surface of the second housing part with a number of inwardly directed locking means that fit into corresponding holes or recesses on the outer surface of the end section 16 when the two housing parts are attached together. The protrusion 20 may then be arranged with interruptions or cutaways so that the inwardly directed locking means may pass. In this context it is to be understood that the protrusion 20, as well as the groove 40 may have interruptions, i.e. need not be continuous along their entire extension, without losing their locking and attaching ability according to the invention.

The arrangement of the connecting structures, i.e. the attachment means, the locking means and the stop members could be varied in many different configurations, such as a protrusion on an inner surface of a housing part mating with a groove on the outer surface of the other housing part without departing from the spirit of the invention.

It is to be understood that the present invention as described and shown may also be modified in many other ways within the scope of protection defined by the patent claims without departing from the inventive idea.

The invention claimed is:

1. A coupling arrangement in a medicament delivery device, the coupling arrangement being configured to permanently attach first and second longitudinally elongated tubular components to each other, and comprising:
   a first positive connection mechanism configured to lock the first and the second tubular components to each other in the medicament delivery device such that the first and second tubular components are locked from being moved in a longitudinal direction in relation to each other; and
   a second positive connection mechanism configured to lock the first and the second tubular components to each other in the medicament delivery device such that the first and second tubular components are locked from being rotated in relation to each other about a longitudinal axis of the first and second tubular components;
   wherein the first positive connection mechanism comprises a first attachment device, a first stop member, a second attachment device, and a second stop member; and the second positive connection mechanism comprises a first locking device and a second locking device;
   the first attachment device, the first locking device, and the first stop member are arranged to the first tubular component in a proximal end section; the first attachment device has a form of at least one first structure that extends helically in circumferential and longitudinal directions;
   the second attachment device, the second locking device, and the second stop member are arranged to the second tubular component in a distal end section; the second attachment device has a form of at least one second structure that extends helically in circumferential and longitudinal directions; and
   the at least one first structure comprises either a first protrusion or a first groove, and the at least one second structure complementarily comprises either a second groove or a second protrusion, wherein either the first protrusion or the second protrusion, whichever is present, has a helical extension with a pitch that causes elliptic deformation of at least one structure during assembly of the first and second tubular components by linear relative movement without rotation.

2. The coupling arrangement of claim 1, wherein the at least one first structure and the at least one second structure comprise complementary attachment surfaces that face each other in generally opposite longitudinal directions such that the complementary attachment surfaces abut each other when the first and second tubular components are attached to each other.

3. The coupling arrangement of claim 2, wherein the complementary attachment surfaces are arranged generally parallel to a plane transverse to the longitudinal axis.

4. The coupling arrangement of claim 2, wherein the complementary attachment surfaces are inclined in relation to a plane transverse to the longitudinal axis of the first and second tubular components, such that undercuts are formed.

5. The coupling arrangement of claim 1, wherein the first stop member comprises a first annular surface facing a proximal direction, and the second stop member comprises a second annular surface facing a distal direction.

6. The coupling arrangement of claim 1, wherein the first locking device forms at least one first longitudinally elongated structure, and the second locking device forms at least one second longitudinally elongated structure.

7. The coupling arrangement of claim 6, wherein the first and second locking devices have complementary shapes configured for mating with each other to form the second positive connection when the first and second tubular components are attached to each other.

8. The coupling arrangement of claim 7, wherein the first locking device has a form of a male or female structure, and the second locking device has a form of a male or female structure complementary to the form of the first locking device.

9. The coupling arrangement of claim 8, wherein the first and the second locking devices comprise ratchets having complementary shapes.

10. The coupling arrangement of claim 1, wherein the first and second tubular components are housing parts of the medicament delivery device.

11. The coupling arrangement of claim 10, wherein the medicament delivery device is a pen-like injector.

12. The coupling arrangement of claim 1, wherein the distal end section of the second tubular component has an elliptical shape when the first and the second tubular components are locked to each other, and the at least one first structure applies force to less than an entirety of a circumference of the elliptical shape when the first and the second tubular components are locked to each other.

\* \* \* \* \*